US012590883B2

(12) United States Patent
Bravo Imaz et al.

(10) Patent No.: US 12,590,883 B2
(45) Date of Patent: Mar. 31, 2026

(54) SYSTEM AND METHOD FOR INSPECTING A FLUID

(71) Applicant: ATTEN2 ADVANCED MONITORING TECHNOLOGIES S.L., Eibar (ES)

(72) Inventors: Iñaki Bravo Imaz, Eibar (ES); Aitor Arnaiz Irigaray, Eibar (ES)

(73) Assignee: ATTEN2 ADVANCED MONITORING TECHNOLOGIES S.L., Eibar (ES)

( * ) Notice: Subject to any disclaimer, the term of this patent is extended or adjusted under 35 U.S.C. 154(b) by 108 days.

(21) Appl. No.: 18/580,046

(22) PCT Filed: Jul. 20, 2021

(86) PCT No.: PCT/ES2021/070540
§ 371 (c)(1),
(2) Date: Jan. 17, 2024

(87) PCT Pub. No.: WO2022/018315
PCT Pub. Date: Jan. 27, 2022

(65) Prior Publication Data
US 2024/0344962 A1 Oct. 17, 2024

(51) Int. Cl.
*G01N 15/1433* (2024.01)
*G01N 11/00* (2006.01)
(Continued)

(52) U.S. Cl.
CPC ......... *G01N 15/1433* (2024.01); *G01N 11/00* (2013.01); *G01N 15/1434* (2013.01);
(Continued)

(58) Field of Classification Search
CPC ............... G01N 11/00; G01N 15/1433; G01N 15/1434; G01N 15/1459; G01N 33/2858;
(Continued)

(56) References Cited

U.S. PATENT DOCUMENTS

| | | | |
|---|---|---|---|
| 9,341,612 B2 | 5/2016 | Gorritxategi et al. | |
| 2006/0024756 A1* | 2/2006 | Tibbe ............... | G01N 33/54333 435/7.2 |
| 2008/0261261 A1* | 10/2008 | Grimes ............. | G01N 33/4905 435/287.1 |

FOREIGN PATENT DOCUMENTS

| | | | | |
|---|---|---|---|---|
| CN | 105784570 A | * | 7/2016 | ........ G01N 15/1031 |
| CN | 110879191 A | * | 3/2020 | ............ G01N 15/00 |

(Continued)

OTHER PUBLICATIONS

Le Bras, Yannick et al. "A new magneto-elastic resonance based technique to determine magneto-mechanical parameters of amorphous ferromagnetic ribbons." Rev. Sci. Instrum. Apr. 1, 2013; 84 (4): 043904. (Year: 2013).*

(Continued)

*Primary Examiner* — Michael A Lyons

(74) *Attorney, Agent, or Firm* — CANTOR COLBURN LLP

(57) ABSTRACT
A system for inspecting a fluid includes a lighting system for illuminating a fluid under inspection in an image detection area; an image capture system for capturing a sequence of images of the fluid in the image detection area; a magnetic component for generating a magnetic field towards the image fluid under inspection, the magnetic component having at least one coil for generating a magnetic field, whereby ferromagnetic particles in the fluid under inspection are prevented from reaching the image detection area; wherein the image capture system is configured to capture an image of the fluid in the image detection area before the magnetic field is applied and an image of the fluid in the image detection area after the magnetic field is applied, free of ferromagnetic particles; and a processing component configured to compare the images of the fluid under inspection and count the ferromagnetic particles in the fluid.

12 Claims, 6 Drawing Sheets

(51) Int. Cl.
　　　*G01N 15/00*　　　(2024.01)
　　　*G01N 15/14*　　　(2024.01)
　　　*G01N 15/1434*　　(2024.01)
　　　*G01N 33/28*　　　(2006.01)

(52) U.S. Cl.
　　　CPC ..... *G01N 15/1459* (2013.01); *G01N 33/2858* (2013.01); *G01N 2011/008* (2013.01); *G01N 2011/0086* (2013.01); *G01N 2015/0053* (2013.01); *G01N 2015/1486* (2013.01)

(58) Field of Classification Search
　　　CPC ..... G01N 2011/008; G01N 2011/0086; G01N 2015/0053; G01N 2015/1486
　　　See application file for complete search history.

(56) References Cited

FOREIGN PATENT DOCUMENTS

| EP | 3348993 | A1 | | 7/2018 | |
|----|---------|-----|---|--------|---|
| WO | WO-9749981 | A1 | * | 12/1997 | ............ G01N 11/16 |
| WO | 2019202132 | A1 | | 10/2019 | |

OTHER PUBLICATIONS

Markova et al., "On-line acoustic viscometry in oil condition monitoring", Tribology International 44 (2011) 963-970.

Ripka et al., "Characterization of Magnetic Wires for Fluxgate Cores", Solid-State Sensors, Actuators and Microsystems Conference, 2007., pp. 2369-2372.

International Search Report for International Application No. PCT/ES2021/070540, dated Oct. 15, 2021, 2 pages.

* cited by examiner

SYSTEM AND METHOD FOR INSPECTING A FLUID

CROSS-REFERENCE TO RELATED APPLICATIONS

This application is a 35 U.S.C. § 371 National Stage patent application of PCT/ES2021/070540, filed on 20 Jul. 2021, the disclosure of which is incorporated herein by reference in its entirety.

TECHNICAL FIELD

The present disclosure relates to the field of fluid monitoring for determining the general condition of fluids, such as their degradation and particle content. This monitoring is for example applicable to lubricating oils, since their state of degradation and particle content provides information on the machinery lubricated by the lubricating oil. More specifically, the present disclosure relates to the monitoring of magnetic particles in a fluid, as well as the viscosity of the fluid, such as in lubricating oil.

BACKGROUND

Industrial machinery often uses lubricating fluids in order for the components of the machine in question to operate correctly. Failures or interruptions in industrial machinery are usually caused by problems associated with lubrication. These failures or interruptions can reduce the service life of the machinery, as well as entail unnecessary maintenance costs. Examples of lubricating fluids include lubricants and oils that can be hydrocarbon-, synthetic product- and/or petroleum-based, as well as hydraulic fluids. These fluids must be kept within a certain composition and cleanliness range for an efficient performance of the machine. For example, the undesired addition of water or residues can cause the machine to lose efficiency and be damaged. Therefore, the fluid, such as lubricating oil, used for lubrication must be monitored because it provides relevant information regarding the machine condition.

In normal operating conditions, lubricant oil forms a film between the moving mechanical components of the machinery, preventing direct contact between them. This film must have a certain thickness, meaning that if the thickness is too large, the mechanical components may be subjected to extra stress, while if it is too low, the mechanical components may be in direct contact, generating excessive heat and possibly damaging the components and producing a malfunction. The property of the lubricant oil that is directly related with the thickness of the oil film is viscosity. A change in oil viscosity is usually a first indication of a more serious problem. Depending on the nature of the fault, oil viscosity may increase or decrease. Therefore, monitoring viscosity potentially enables the detection of premature failures, preventing more serious faults. Thus, it is recommended to monitor lubricant oil viscosity, as it is directly related with the thickness of oil film between lubricated mechanical components, which in turn is the origin of many faults that may lead to catastrophic failures. There are however malfunctioning situations in which oil viscosity doesn't change.

A conventional way of monitoring the state of the lubricating oil is by off-line measurement, that is, by analyzing oil samples in a laboratory. However, off-line techniques do not provide an early enough detection of the degradation process mainly because collecting and analyzing samples is not done frequently enough.

In order to overcome the drawbacks inherent to off-line analysis techniques, on-line techniques have been developed in order to evaluate the state of a fluid during the operation thereof, when in motion, without the need to extract samples thereof for its subsequent analysis and without losing production time. For example, U.S. Pat. No. 9,341,612B2 discloses a system for inspecting oil, which comprises a cell through which oil flows along a pipe. A lighting system having a LED diode supplies a light beam to the flow of oil. An image capture system situated on the opposite side of the pipe in respect of the lighting system captures a sequence of images of the oil flowing inside the pipe. By processing the captured images, the presence of particles in the oil and an index of oil degradation are determined.

In certain situations, for example when the instant velocity of the particles comprised in the oil is relatively high, the system disclosed in U.S. Pat. No. 9,341,612B2 may be unable to capture an image of some particles or may be able to capture an image but the morphology of the particles may be incorrectly determined, in other words, particles may be distorted. This problem is addressed by EP3348993A1, which discloses a system for detecting microscopic objects in a flowing fluid, in which a lighting system supplies high power light pulses having very short time duration. The time instant at which the light pulses are triggered is synchronized with the time instants at which pixels in an image capture system start to capture each image frame. The amplitude and time duration of the light pulses is controlled from information obtained from the captured image frames.

On the other hand, particles comprised within a fluid, such as lubricating or hydraulic fluid, can be classified as metallic ones and non-metallic ones. Metallic particles within a lubricant or hydraulic fluid are directly related to the contact between two metallic bodies and thus to the degradation of the metallic bodies. Therefore, it is desirable to count or measure metallic particles because they provide relevant information about the state—also referred to as health state—of the machinery in contact with the lubricant or hydraulic fluid. Non-metallic particles usually have a different origin from metallic ones. They may for example be caused by seals or dirt. Non-metallic particles may provide relevant information because they are associated with diverse faults or problems, such as contamination of the lubricant or hydraulic fluid and degradation of different parts of the machinery, such as seals. However, the presence of non-metallic particles may distort the measurements associated to metallic ones and generate an inaccurate health index. A very interesting property of most common metallic materials used in engineering, for example steel, is ferromagnetism. Ferromagnetism is the property by which certain materials (such as iron) are attracted to magnetic fields. So, by applying a magnetic field, ferromagnetic particles can be attracted. Therefore, there is a need for a system and method for inspecting a fluid which overcomes the former drawbacks.

SUMMARY

The drawbacks of conventional systems and methods for inspecting fluids and detecting objects or particles in a fluid, such as lubricating oil, are solved by the present disclosure, which provides a system and method for inspecting a fluid. In the system and method of the present disclosure, ferromagnetic particles are eliminated from (or prevented to reach) the image detection area. This makes the counting and classification of particles more precise. The quality of the information on the health state of the asset on which the fluid is working is thus improved.

In particular, two images of the fluid under inspection may be taken: One image of the fluid—including both ferromagnetic and non-ferromagnetic particles—under inspection is captured at an image detection area. Another image of the fluid is taken at the image detection area after removing—by attraction—ferromagnetic particles comprised within the fluid. This is done by applying a magnetic field. The order of the image taking may be altered. By applying a computing algorithm for comparing the two images, the ferromagnetic particles are identified. For example, by subtracting the ferromagnetic particles from the total amount of particles, the number of ferromagnetic particles can be estimated (and therefore also the number of non-ferromagnetic particles).

The magnetic field for attracting the ferromagnetic particles from the fluid occupying the image detection area is applied by magnetic means. In embodiments of the disclosure, the magnetic means is at least one coil. In embodiments of the disclosure, the magnetic means is a magnetic viscosimeter, in particular a magnetoelastic sensor implementing a micro-vibration-based technique for measuring viscosity. The advantage of including a magnetoelastic sensor within the system for inspecting a fluid, is that it enables both the removal of ferromagnetic particles from the fluid under inspection—in particular from the image detection area, which is also the area exposed to the magnetic field, and the measurement of the fluid viscosity.

Therefore, the proposed system and method permit to accurately assess the quality of the fluid under inspection by measuring the number of ferromagnetic and non-ferromagnetic particles present within the fluid, as well as its viscosity, thus obtaining accurate information about the state of the machinery in contact with the lubricant or hydraulic fluid.

In a first aspect of the present disclosure, a system for inspecting a fluid is provided. The system comprises a lighting system for illuminating a fluid under inspection in an image detection area; an image capture system for capturing a sequence of images of the fluid in the image detection area; magnetic means for generating a magnetic field towards the image fluid under inspection, the magnetic means comprising at least one coil for generating a magnetic field, such that ferromagnetic particles comprised in the fluid under inspection are prevented from reaching—or removed from—the image detection area; wherein the image capture system is configured to capture an image of the fluid located in the image detection area before the magnetic field is applied and an image of the fluid located in the image detection area after the magnetic field is applied, therefore free of ferromagnetic particles; processing means configured to compare said images of the fluid under inspection and count the ferromagnetic particles comprised in the fluid.

In embodiments of the disclosure, the system further comprises a diffuser situated between the lighting system and the fluid under inspection, configured to provide homogeneous lighting to the area to be illuminated.

In embodiments of the disclosure, the system further comprises a lens situated between the image capture system and the fluid under inspection, configured to focus the captured images.

In embodiments of the disclosure, the magnetic means further comprises means for measuring viscosity implementing a micro-vibration based technique.

In embodiments of the disclosure, the magnetic means comprises: a first coil configured to generate an alternating magnetic field; a magnetoelastic strip submerged in the fluid under inspection and configured to be excited by the alternating magnetic field generated by the first coil and to produce magnetoelastic resonance; a second coil in which voltages related to the magnetoelastic resonance of the magnetoelastic strip are induced within a range of frequencies; measuring means configured to measure said induced voltages at said range of frequencies; wherein the processing means is further configured to obtain the viscosity of the fluid from at least one parameter obtained from said induced voltages and frequencies, said at least one parameter being one of: the amplitude of the magnetoelastic resonance, the amplitude of the magnetoelastic antiresonance, the frequency of the magnetoelastic resonance, frequency of the magnetoelastic anti resonance, the damping of the magnetoelastic resonance curve and the damping of the magnetoelastic antiresonance curve.

In embodiments of the disclosure, the system further comprises a compensation coil for suppressing magnetic noise generated by the first coil.

In embodiments of the disclosure, the compensation coil is disposed in series—but wounded in opposite direction—with the second coil.

In embodiments of the disclosure, the system further comprises at least one additional coil for setting the bias field for the magneto-elastic strip.

In embodiments of the disclosure, the coil for generating a magnetic field towards the fluid under inspection for attracting ferromagnetic particles, is the at least one additional coil of the means for measuring viscosity.

In embodiments of the disclosure, the magneto-elastic strip is surrounded by the second coil, which in turn is surrounded by the first coil, which in turn is surrounded by the at least one additional coil.

The system for inspecting a fluid of the present disclosure may be a sub-system or module of a larger system or installation comprising several sub-systems connected to each other and contained within a receptacle or container. The inspection system is an autonomous sub-system with totally independent functioning, which delivers auto interpretable measurements, calibrated and corrected for the entire defined operating range. In other words, it delivers measurement values that have no need of further processing. The inspection system may be designed to be installed in a by-pass of a lubricating system of certain machinery. Fluid circulation is enabled thanks to pressure differences. Others sub-systems of the complete installation may be a hydraulic conditioning sub-system including flow control components, such as electro-valves, pressure control, filters and inlet and outlet piping; and an electronic sub-system for managing all active sub-systems, managing data channels and including internal and external connection technologies and power system.

The system for inspecting a fluid of the present disclosure may operate on a micromechanical cell through which the fluid under supervision circulates. The fluid is preferably oil, more preferably lubricating oil. The fluid is driven inside channeling means, such as for example a pipe. The system for inspecting a fluid, such as oil, of the present disclosure may alternatively operate in a take-off of a container.

In a second aspect of the present disclosure, a method for inspecting a fluid is provided. The method comprises: illuminating a detection area having a fluid having particles suspended thereon; capturing an image of the fluid in the detection area; generating a magnetic field towards the image detection area, in such a way that ferromagnetic particles comprised in the fluid are removed from—or prevented from reaching—the image detection area; capturing an image of the fluid, free of ferromagnetic particles—in the detection area; comparing said images of the fluid and counting the ferromagnetic particles comprised in the fluid.

In embodiments of the disclosure, the method further comprises measuring the viscosity of the fluid as follows: generating an alternating magnetic field at a first coil; exciting a magnetoelastic strip submerged in the fluid under inspection, thus producing magnetoelastic resonance; in a second coil, inducing voltages related to the magnetoelastic resonance of the magnetoelastic strip within a range of frequencies; measuring said induced voltages at said range of frequencies; obtaining the viscosity of the fluid from at least one parameter obtained from said induced voltages and frequencies, said at least one parameter being one of: the amplitude of the magnetoelastic resonance, the amplitude of the magnetoelastic antiresonance, the frequency of the magnetoelastic resonance, frequency of the magnetoelastic anti resonance, the damping of the magnetoelastic resonance curve and the damping of the magnetoelastic antiresonance curve.

In a third aspect of the present disclosure, a computer program comprising computer program code means adapted to perform the following steps when said program is run on a computer, a digital signal processor, a field-programmable gate array, an application-specific integrated circuit, a microprocessor, a micro-controller, or any other form of programmable hardware, is provided: generating an alternating magnetic field at a first coil; exciting a magnetoelastic strip submerged in the fluid under inspection, thus producing magnetoelastic resonance; in a second coil, inducing voltages related to the magnetoelastic resonance of the magnetoelastic strip within a range of frequencies; measuring said induced voltages at said range of frequencies; obtaining the viscosity of the fluid from at least one parameter obtained from said induced voltages and frequencies, said at least one parameter being one of: the amplitude of the magnetoelastic resonance, the amplitude of the magnetoelastic antiresonance, the frequency of the magnetoelastic resonance, frequency of the magnetoelastic anti resonance, the damping of the magnetoelastic resonance curve and the damping of the magnetoelastic antiresonance curve.

In sum, the proposed system and method permit to obtain accurate information about the state of the machinery in contact with the lubricant or hydraulic fluid, by detecting and counting the ferromagnetic particles on the one hand, and the non-ferromagnetic particles on the other hand, travelling/located within the fluid under inspection, as well as the viscosity of the fluid. The obtained information permits to prematurely detect potential failures that, if not handled in time, may lead to catastrophic failures. All this is done in a small compact system that can be installed in a by-pass of a lubricating system of certain machinery. The system may operate on a micromechanical cell through which the fluid under supervision circulates.

Additional advantages and features of the disclosure will become apparent from the detail description that follows and will be particularly pointed out in the appended claims.

BRIEF DESCRIPTION OF THE DRAWINGS

As a complement to the description and with a view to contributing towards an improved understanding of the characteristics of the disclosure, according to an example of a practical example thereof, a set of drawings is attached as an integral part of this description, which by way of illustration and not limitation, represent the following.

DETAILED DESCRIPTION OF THE DRAWINGS

Figure 1:
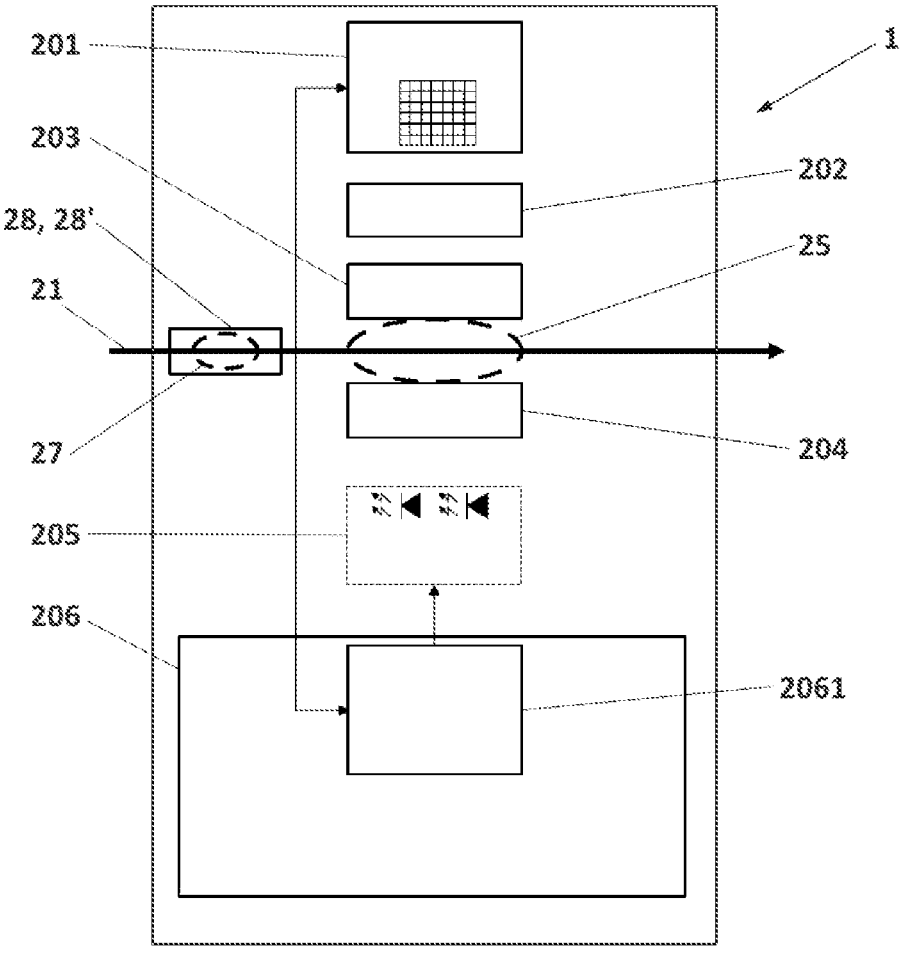
FIG. 1 schematically represents a system for inspecting a fluid according to an embodiment of the disclosure.
Figures 2A, 2B:
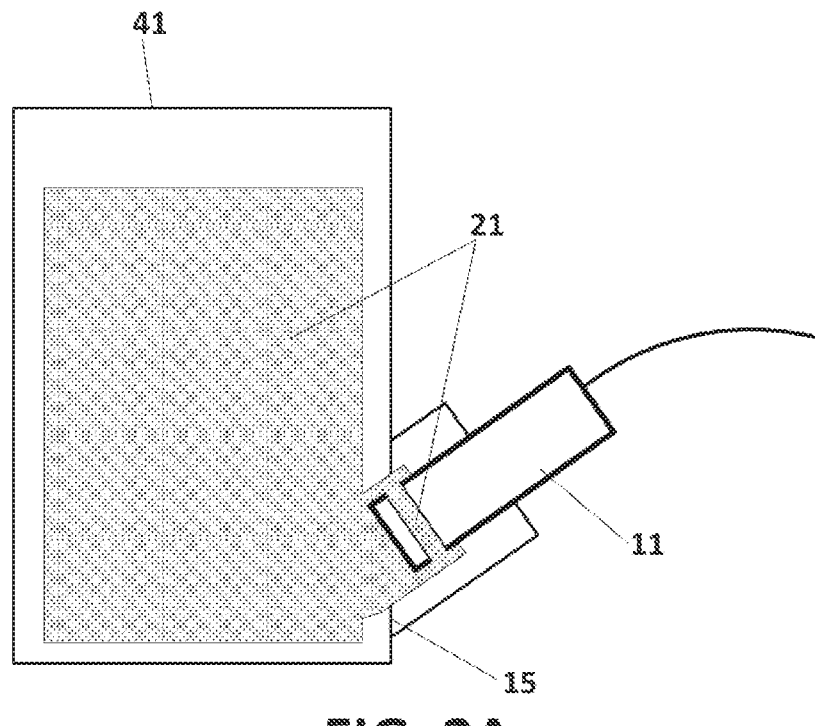
FIG. 2A schematically shows a system for inspecting a fluid in which the system is inserted in a simple take off of a tank containing the fluid, according to an embodiment of the disclosure.
FIGS. 2B and 2C show two views—front and profile, respectively—of the inspection system according to a possible embodiment of the disclosure. In these views, the channel through which the sample under inspection flows or is disposed can be seen. One part of the fluid contained in the tank in which the inspection system is coupled, circulates through (or is located in) this channel.

FIGS. 1 and 2A-2D show different implementations of systems for inspecting a fluid. The fluid may be, for example, a lubricating or hydraulic fluid. The monitoring or inspecting system is sometimes referred to as sensor throughout the present disclosure. At the monitoring system 1 shown in FIG. 1, measurements of a moving fluid are usually taken. System 1 is designed for its direct integration into a lubricating system of machinery without affecting the operating conditions thereof. This is achieved by a hydraulic sub-system (not shown) which enables controlled sampling in lubricating fluid (for example, oil) by in-line installation. The fluid 21 may be driven inside channeling means, for example a regular pipe, and circulates thanks to a small pressure difference between the input and the output of the system (0.05 Bar or larger is usually enough). System 1 may operate on a micromechanical cell through which the fluid 21 under supervision circulates. In this case, illustrated in FIG. 1, the fluid 21 under supervision may circulate inside a pipe within the micromechanical cell, generally represented by system 1. In the monitoring system 11 shown in FIGS. 2A-2D, the fluid is measured by coupling the system to a tank containing the fluid. For example, as shown in FIG. 2A, the system 11 may be coupled to a tank, reservoir or pipe 41 containing the fluid 21 under inspection, through a simple take off 15, such as a standard hydraulic take off. Thus, the need to carry out a bypass by means of conduits or pipes diverting the fluid 21 for its monitoring is avoided. The fluid may be substantially static or in motion. In any embodiment (FIGS. 1 and 2A-2D), the system 1, 11 can take measurements of the fluid 21 without needing to extract a fluid sample from the reservoir or installation. Communication interfaces and power supply units are also typically used. The system 1, 11 is of small size and compact in order to be fitted if required within larger hydraulic subsystems, such as filters or valves. Fluid is preferably oil, such as lubricating or hydraulic oil.

Figure 2C:
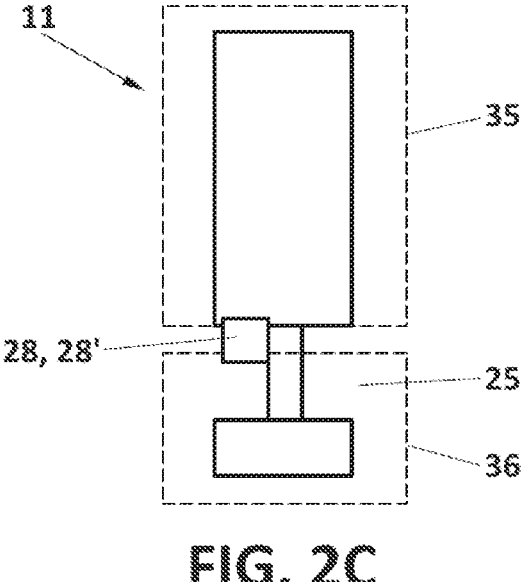
Figure 2D:
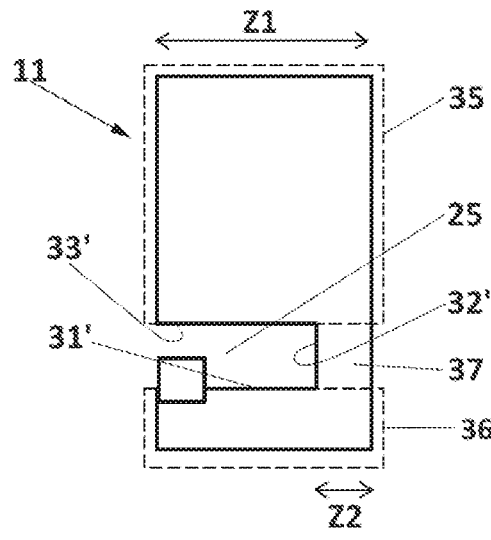
FIG. 2D shows a profile view of an inspection system according to another embodiment of the disclosure, wherein the channel is formed outside the system. The channel is built as a narrow portion of the housing of the system.

FIGS. 2B and 2C show front and profile views, respectively, of a possible implementation of system 11. A casing, case or cover has a shape that enables the passage or presence of the fluid 21 between four outer surfaces 31, 32, 33, 34 of the casing. That is, the fluid 21 passes through or fills an area 25 that is outside the casing. This outer area is a type of tunnel, channel, conduit or measuring area between an outer surface of a first portion 35 of the casing and an outer surface of a second portion 36 of the casing facing the first portion 35 of the casing, both portions defining the conduit or measuring area 25 for the fluid 21. The second portion 36 is U-shaped, this shape defining the channel 25 through which the fluid 21 flows or remains when the inspection system 11 has been coupled to the reservoir 41 of the fluid 21 under supervision. FIG. 2D shows a profile view of another possible implementation of the monitoring system 11. As in the previous case, the casing, case or cover of the system or sensor 11 has a shape that enables the passage of the fluid 21 between three outer surfaces 31', 32', 33' of the casing. These three surfaces 31' 32' 33' define the channel between an outer surface of a first portion 35 of the casing and an outer surface of a second portion 36 of the casing facing the first portion 35 of the casing, both portions defining the conduit or channel for the fluid 21. That is, as can be seen in FIG. 2D, the casing has a specific dimension (e.g. width) "z1" in the first and second portions, but is narrower (width "z2") in an intermediate portion 37 between the first and second portions 35 36, such that the casing is divided into two portions joined by a narrow part 37 of the casing, there being a gap or channel 320 through which the fluid 21 flows or remains when the monitoring system 11 has been coupled to the reservoir 41 of the fluid 21 under supervision. Although in FIGS. 2B-2D the surface that delimits the channel (measuring area) 25 has been shown as walls or flat surfaces (31-34, 31'-33'), other implementations of the casing can be carried out with curved surfaces, for example a substantially curved surface, wherein a clear differentiation cannot therefore be made between said surfaces 31-34 or 31'-33'.

Depending on the configuration of the reservoir 41 that contains the fluid 21 under analysis, the take-off or coupling 15 in the reservoir 41, through which the sensor or monitoring system 11 is inserted or coupled in the reservoir 41, can be on one side of the reservoir 41, as is the case with the configuration shown in FIG. 2A, or can be in the upper part (for example, lid) of the reservoir 41. In the first case, the monitoring system 11 is inserted in the reservoir 41 obliquely to the same. In the second case, the monitoring system 11 is inserted in the reservoir 41 perpendicularly thereto.

In the implementations shown in FIGS. 2A-2D, in which system 11 is coupled to a reservoir 41, the fluid under inspection (in measuring area 25) can be considered substantially static, although it may also be in motion. It may be in motion when system 11 is coupled to a pipe. In the implementation shown in FIG. 1, the fluid under inspection is usually a fluid in motion, travelling along the inspection area 25.

The following description of the system 1, 11 for inspecting a fluid is applicable to any of the embodiments shown in FIGS. 1, 2A-2D. It is noted that in FIGS. 2A-2D specific elements of the inspection system are not shown only for simplicity. System 1, 11 comprises an optical part and an electronic part—also referred to as video acquisition and processing sub-system. The optical part has a lighting system 205 for emitting a light beam to the flowing fluid 21. Then, an image capture system 201 of the video acquisition and processing sub-system captures a video sequence of an image detection area 25, which is an area occupied by flowing fluid 21 illuminated by the light beam. The lighting system 205 may be based on one or more LED diodes (LED emitters) which light, either continuously or at regular flashes of light, the flowing fluid 21 which travels through the measuring area (image detection area) 25. In applications in which the instant velocity of the particles comprised in the fluid 21 is relatively high, the lighting system 205 may be a stroboscopic lighting system where light pulses are synchronized with the video capture. A diffuser 204 may be disposed between the lighting system 205 and the flow of fluid 21 along measuring area 25, for diffusing the amount of light emitted by the lighting system 205 in order to obtain a homogenous lighting over the entire area 25—amount of fluid—that is being inspected. The lighting system 205 may comprise other elements, such as a control system, which is out of the scope of the present disclosure. An embedded processor 2061 may control the lighting system 205. In the system 1 of FIG. 1, there may be two windows 203, 204 made of a transparent material substantially delimiting the area 25 illuminated by the lighting system 205 and within the detection field of the image capture system 201. Window 203 may be a calibration window which comprises markings or patterns that allow it to be auto-calibrated, as explained in U.S. Pat. No. 9,341,612B2, which is herein incorporated by reference. As taught in U.S. Pat. No. 9,341,612B2, the video acquisition and processing sub-system applies algorithms for the dimensional calibration of system 1.

Opposite the lighting system 205, on the other side of the measuring area 25 through which the fluid 21 circulates, an image capture system 201, for example based on CMOS sensor or on a CCD camera, is located. When the system 11 of FIGS. 2A-2D is used, the lighting system 205 is for example within portion 35 of the system 11 and the image capture system 201 within portion 36 thereof, or vice versa. The image capture system 201 captures the video sequence—a train of images—of the zone of interest in the passage of the fluid. The image capture system 201 is capable of determining a defined minimum size of particle taking into account several conditions, such as, when the fluid is not static, the instant velocity of the fluid in which the particles are suspended. Depending on different conditions, such as the instant velocity and the opacity of the fluid, the minimum size of particle to be measured may be, for example, 0.1 μm, over an inspection area of several mm², such as about 100 mm². The resolution is achieved by optimising several conditions, such as the area to be inspected, the size of the camera, its number of pixels and characteristics of lens 202 (if there is one). An optional lens 202 may be used for transporting the image from the object to the camera 201. The video acquisition and processing sub-system carries out the activities related to measurements, among other things. It is comprised of an embedded image capture system 201 and electronics 206. Electronics 206 comprises processing means 2061, such as an embedded processor, preferably disposed in the proximity of the lighting system 205. Images (video sequence) of the fluid 21 captured by the camera are processed at processing means 2061, such as a DSP device or a CPU, which analyses the images. The goal of the processing is to determine the presence of particles and/or bubbles and the degradation value of the fluid due to the particles; to determine the shape of the particles; and/or to establish the viscosity of the fluid. For this purpose, processing means 2061 comprises software means that may include algorithms for the detection and classification of particles, bubble detection, determination of degradation and determination of viscosity. Processing means 2061 can analyse, for each image, whether there are bubbles and particles, count them, determine the size and shape of the detected objects (bubbles and particles) and calculate the viscosity of the fluid. It can also classify particles as ferromagnetic or non-ferromagnetic particles, as explained next. The system also includes conventional components, such as communication interface, power source and memory. The distance between the object—plane of passage of the fluid under inspection—and the image capture system 201 is desirably as short as possible and does not exceed approximately 40 mm, so that the system can be as compact and small as possible.

The system 1, 11 for inspecting a fluid also permits to identify and count ferromagnetic particles comprised in the fluid 21 under inspection. Specifically identifying the ferromagnetic particles travelling or located within the fluid 21 is important in order to evaluate the health state of the machinery in contact with the lubricant or hydraulic fluid. In particular, it is important to determine the amount of ferromagnetic particles with respect to the total amount of particles (ferromagnetic and non-ferromagnetic) because the presence of non-ferromagnetic particles may distort the measurements associated to ferromagnetic ones and generate a wrong impression of the health state of the machinery under evaluation. As a matter of example, non-ferromagnetic particles, such as sand or dust particles, do not in principle relate to the degradation state of the machinery.

Figure 3A:
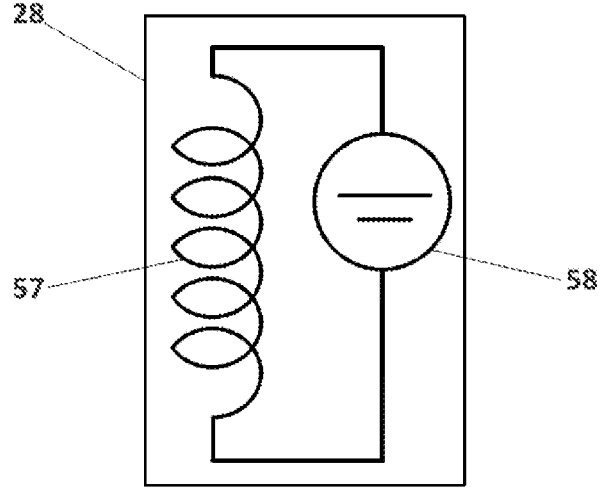
FIG. 3A shows a possible implementation of magnetic means for applying a magnetic field for attracting ferromagnetic particles, according to an embodiment of the disclosure.
Figure 4:
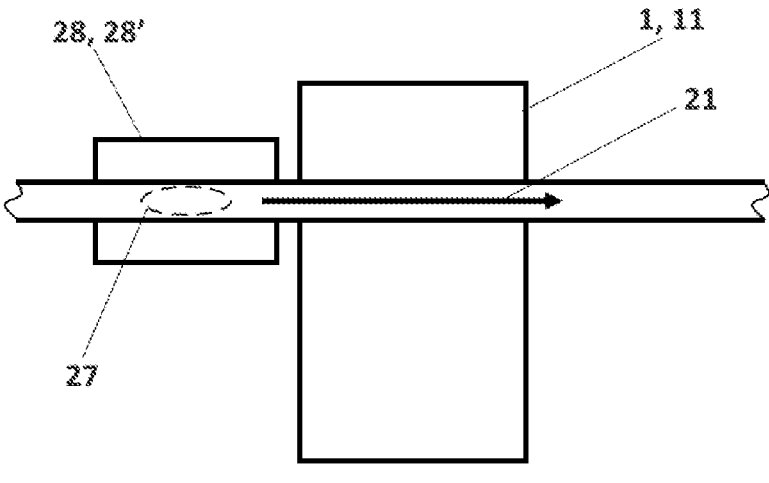
FIG. 4 shows a possible implementation of the magnetic means with respect to the measuring system.

In order to monitor the ferromagnetic particles comprised within the fluid 21, magnetic means 28 for applying a magnetic field towards the fluid under inspection, is used. This way, the ferromagnetic particles comprised in the fluid 21 and travelling through or comprised within the detection area 25 are attracted away the detection area 25, that is to say, eliminated from the portion of fluid 21 situated within the detection area 25. Magnetic means 28 is located in the vicinity of the detection area 25. For example, in the system 1 in FIG. 1, magnetic means 28 is located before the detection area 25 with respect to the direction of flow of fluid. In FIGS. 2B and 2D, the magnetic means 28 is located in the vicinity of the detection area 25 provided that the magnetic means manages to attract the ferromagnetic particles present in the fluid under inspection. Magnetic means 28 may be implemented within the measuring system (within the micromechanical cell illustrated in FIG. 1 or within the sensor 11 illustrated in FIGS. 2A-2D), or as a separate part with respect to the measuring system, as illustrated in FIG. 4. In any implementation, magnetic means 28 is configured to attract ferromagnetic particles in order to prevent them from reaching the detection area 25 (or to remove them from the detection area 25 in the event they are already there). The magnetic field is generated in such a way that the direction of the magnetic field drags the ferromagnetic particles out of the vision field (detection area 25) of the particle counting sensor—the image capture system 201. Ferromagnetic particles react to the applied magnetic field by aligning and moving in the direction of the field. FIG. 3A shows a possible implementation of magnetic means 28, which comprises a coil 57 and a voltage or current source 58 for switching on/off the magnetic means 28. Preferably, source 58 is a DC source. Alternatively, it may be an AC source. Source 58 may be a source dedicated to the magnetic means 28, in which case it may be located within magnetic means 28; or it may be provided by the general power supply of system 1, 11. Although not shown, magnetic means 28 may comprise two coils 57, which may simplify the design of the system 1, 11.

The operation is as follows. The image capture system 201 captures an image of the fluid 21 flowing or located through the image detection area 25. The image of the fluid—comprising ferromagnetic and non-ferromagnetic particles present in the fluid—is stored in memory means preferably comprised in electronics 206. The particles may then be counted and classified by size and form following conventional algorithms, such as the ones disclosed in EP3348993A1 or in U.S. Pat. No. 9,341,612B2. Once this first image (first picture) is captured, the magnetic means 28 is turned on and applies a magnetic field towards the detection area 25 for attracting the ferromagnetic particles comprised in the fluid 21 away the detection area 25. For example, in FIGS. 1 and 4 magnetic particles are attracted at area 27 within means 28. When ferromagnetic particles are prevented from reaching detection area 25 due to the magnetic field (in other words, when they are removed from the portion of fluid situated within the detection area 25), a new image (second picture) of area 25, this time substantially free of ferromagnetic particles, is captured by the image capture system 201. In other words, a new measurement—image—is made of the fluid once the fluid does not have ferromagnetic particles. By comparing both images, the particles that have disappeared from the first measurement captured prior to applying the magnetic field, may be identified by an algorithm for particle counting and optional analysis. These particles are substantially the ferromagnetic ones.

The two images may be taken in the opposite order. That is to say, first the magnetic means 28 is turned on, in such a way that the first picture of the fluid (free of ferromagnetic particles) is taken. And then the magnetic means 28 is turned off and the second image of the fluid (including ferromagnetic particles) is taken.

Both images are then compared, obtaining the number of identified particles (ferromagnetic and non-ferromagnetic) for each case. In embodiments of the disclosure, processing unit 2061 applies an algorithm for comparing the two images or measurements. Subtracting the number of particles obtained in the picture free of ferromagnetic particles from the total number of particles identified in the other picture, the number of ferromagnetic particles is obtained. If an analysis of shape is done to both images, in addition of the ferromagnetic analysis of the particles detected, more accurate information on the origin and of the particles is obtained. For example, if the shape of the particles in the first and the second image is obtained, in an analogue way, the origin of the ferromagnetic particles is obtained. The result of this algorithm is the number of ferromagnetic particles, optionally classified by sizes and its origin (if analysis by shape has additionally been made).

The fluid within the detection area 25 may be substantially static or in motion. When it is static, the two pictures undoubtedly correspond to substantially the same portion of fluid. When the fluid is in motion, such as in the implementation of FIG. 1, the two pictures may correspond to substantially different portions of fluid. However, it is assumed that the fluid is sufficiently homogeneous so as to consider that from a statistical point of view, the two pictures represent the same fluid in terms of ferromagnetic and non-ferromagnetic particles comprised therein.

Figure 3B:
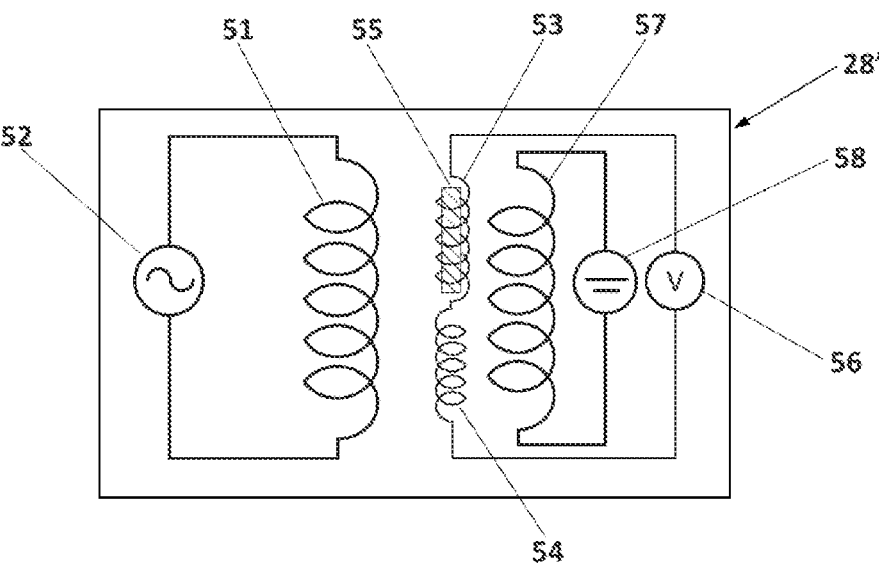
FIG. 3B shows another implementation of magnetic means, which not only attracts ferromagnetic particles, but also measures viscosity of the fluid, according to an embodiment of the disclosure.

In a particular embodiment, the magnetic means also measures viscosity. FIG. 3B schematically shows an apparatus 28' implementing such magnetic means according to an embodiment of the disclosure. The means for measuring viscosity implemented in apparatus 28' is based on vibration techniques, because vibration techniques can be implemented in on-line measurements, such as the ones schematically shown in FIGS. 1 and 2A-2D. In particular, apparatus 28' is a magneto-elastic sensor implementing a micro-vibration based technique for measuring viscosity. Therefore, the magneto-elastic sensor measures a wide range of viscosities of the fluid—such as lubricant oil—on-line, in-situ and in real time. In general, an excitation produced by a magneto-elastic material is generated by an alternating magnetic field that, depending on the frequency and the characteristics of the material, produces forced mechanical oscillations or mechanical resonances. Different materials and sizes can be used for the vibrating element, such as a magneto-elastic ribbon (strip), which is the element that vibrates. The presence of a dissipative force-caused by the fluid under inspection—produces an attenuation of the forced oscillations or a reduction of the magnitude and quality factor of the resonance, which can be correlated to the viscosity of the fluid. Apparatus 28' may be powered with the same power source of system 1, 11. Alternatively, it may be powered with an independent power source (source 52 and/or source 58) in which case it can be commercialized with independence of monitoring system 1, 11.

Magneto-elasticity refers to the magnetization changes caused by the mechanical deformation of a ferromagnetic material. In particular, in a magneto-elastic material, the magnetic permeability of the material depends on the applied stress. The magneto-elastic coupling makes that a stress perturbation (mechanical or sound wave) travelling through a magneto-elastic material, is accompanied by a corresponding magnetic perturbation, building up a magneto-elastic wave. Due to its dual nature, magneto-elastic waves can be generated either mechanically or magnetically inside the material and detected likewise.

When magneto-elastic waves are excited in a bounded material—for instance in a ribbon 55 (thin ribbon) of a given length, as shown in FIG. 3B, stationary waves can be produced if the wavelength of the mechanical oscillation matches the length of the bounded material. This situation produces sharp resonances at which large strains and magnetization changes take place. The effect is called magneto-elastic resonance (MER) and is the core of the detection technology proposed for the detection of the fluid viscosity.

In the magneto-elastic resonance of a ferromagnetic material, the resonant frequency is determined by the value of Young's modulus, that is to say, the Young modulus at given value of the applied magnetic field. Therefore, the resonant frequency can be varied at wish, within a certain range, by magnetically biasing the sample by a controllable magnetic field. The phenomenon behind this tuning capability is the so-called ΔE effect, wherein E refers to the elasticity of the sample. The ΔE effect modifies the resonance conditions. In this sense, not only the resonance frequency of the magneto-elastic ribbon depends on the applied bias field, but also the amplitude of the resonance and the response to temperature. For this reason, in order to maximize the detection capability and eliminate undesirable temperature effects, a bias magnetic field is preferably applied to magnetize the sample in the optimum operating point on the magnetization curve. The suitable bias field is provided by an additional coil (coil 57). Alternatively, it may be provided by a magnet, not shown.

A set-up for measuring the magneto-elastic resonance of a ferromagnetic material must have the capability of producing a bias field (a magnetic excitation in the ferromagnetic material) and of detecting its magnetic response. The apparatus 28' for measuring the viscosity of a fluid through the magneto-elastic resonance of a ferromagnetic material also attracts ferromagnetic particles in a similar way as described with reference to the magnetic means 28. A magneto elastic-strip 55, also referred to as magneto-elastic ribbon 55, is submerged in the fluid 21 under inspection, which viscosity is going to be measured. In this embodiment, a bias field is applied by an external coil 57, which in FIG. 3B is fed by source 58 (voltage or current source). An excitation is generated by an excitation coil 51. The excitation is a constant current signal, with a varying frequency, obtained with an alternating current (AC) source 52. For the measurement of the answer of the magneto elastic strip 55 to this excitation, at least one coil 53 is used. Optionally, a second coil 54 may be used to compensate magnetic noise generated mainly by the excitation coil 51. In coil 53 (pick-up coil or measuring coil) a voltage related to the magnetoelastic resonance of the magnetoelastic strip 55 is induced within a range of frequencies. This range of frequencies is selected depending on the characteristics of strip 55, in particular, depending on its material, size and shape. The selected frequencies must be such that they comprise at least the resonance frequency of the strip 55. Preferably, also the antiresonance frequency of the strip 55 is comprised within the selected range.

In the proposed apparatus 28', the capability of producing a bias field (a magnetic excitation in the ferromagnetic material of ribbon 55) and of detecting its magnetic response, is preferably implemented using at least four coils: a primary coil 51, also referred to as excitation coil, which is fed with an AC from a AC source 52; a secondary coil (or pick-up coil or measuring coil) 53, in which a voltage related to (caused by) magnetization changes in ribbon (strip) 55 is induced; a compensation coil 54, that eliminates electrical noise in the measurement; and at least one coil 57 setting the bias field for the magneto-elastic material. The different voltage values induced in coil 53 at the selected range of frequencies is measured by measuring means 56, such as a voltmeter 56. Thus, a curve of voltage values with respect to frequency values is obtained. This curve may provide, in particular: the amplitude of the magnetoelastic resonance (represented by the maximum voltage in the curve); the amplitude of the magnetoelastic antiresonance (represented by the minimum voltage in the curve); the respective frequencies of the magnetoelastic resonance and antiresonance (frequencies at which maximum and minimum voltages are respectively obtained); and damping values associated to the width of the resonance curve and/or antiresonance curve.

Then, processing means (such as processing means 2061 of system 1, 11 or processing means—not shown—comprised within apparatus 28') applies al algorithm for obtaining the viscosity of the fluid under inspection from at least one of the obtained parameters. That is to say, from at least one of the amplitude of the magnetoelastic resonance (represented by the maximum voltage in the curve); the amplitude of the magnetoelastic antiresonance (represented by the minimum voltage in the curve); the respective frequencies of the magnetoelastic resonance and antiresonance (frequencies at which maximum and minimum voltages are respectively obtained); and damping values associated to the width of the resonance curve and/or antiresonance curve. The algorithm for calculating the viscosity of the fluid is out of the present disclosure.

Compensation coil 54 is disposed in series—but wounded in opposite direction—with the pick-up coil 53 in order to suppress the voltage induced directly by the excitation coil 51, as well as any other background signal/noise. In this way, the signal to noise ratio is considerably improved.

In apparatus 28', the magnetic field that attracts ferromagnetic particles is generated using coil 57, when source 58 is switched on. After a current generated by source 58 passes through this coil 57, a magnetic field is generated. Coil 57 is designed such that the magnetic field is maximum in the middle of coil 57, so ferromagnetic particles will be attracted towards area 27. The ferromagnetic particles react to the magnetic field generated, moving on the direction of the field. This displaces the ferromagnetic particles from the field of operation of the image capture system 201. The viscosity of the fluid 21 is measured by setting the bias field in an optimum position for the magneto-elastic ribbon 55. After this, primary coil 51 excites the ribbon 55 by conducting a voltage with a variable frequency through it. The answer to this excitation is measured in coils 53 and 54. From that measured answer, measured for example using voltmeter 56, the resonant frequency and the anti-resonant frequency, the amplitude of the resonance and antiresonance and the damping of the resonance and antiresonance curves are obtained. This may be done at electronics 206, since apparatus 28, 28' is preferably connected to system 1, 11 through an electrical interface (i.e. wired interface), or at specific processing means comprised in apparatus 28'. These parameters are directly related with the viscosity of the fluid 21, as a person skilled in the art is aware of. Therefore, the apparatus 28' enables the measuring and counting of ferromagnetic particles in the fluid under inspection as well as the viscosity of the fluid.

Figure 5A:
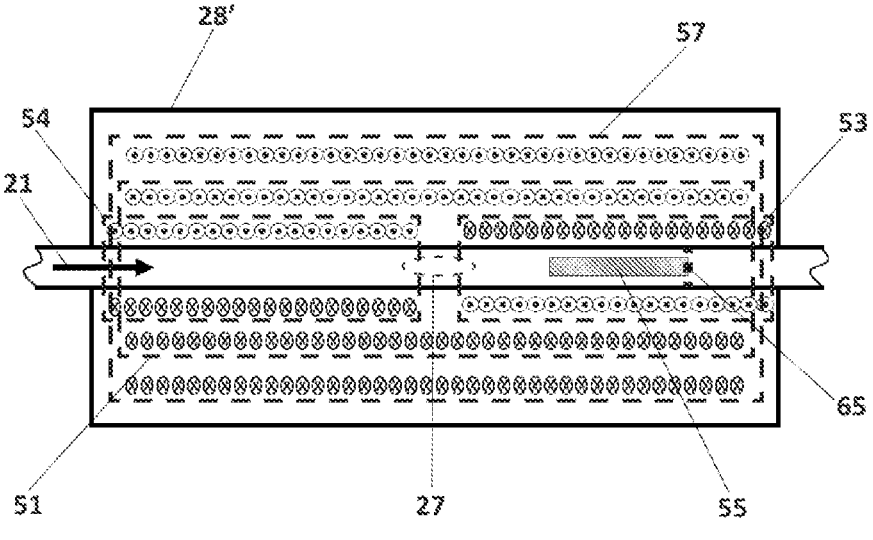
FIG. 5A shows a cross-sectional view of the magnetic means of FIG. 3B.

FIG. 5A shows an embodiment in which the apparatus 28' comprising coils 51, 53, 54, 57 is designed in such a way that the fluid 21 and the magneto-elastic ribbon 55 are placed inside the coils, which concentrically surround the fluid and ribbon. This enlarges the effect of the excitation and the level of the induced signal as much as possible, therefore maximizing the performance of the measuring set-up. As shown in the cross-sectional view of FIG. 5A, apparatus 28' is disposed in contact with the fluid 21 to be monitored. In particular, in this embodiment, along its flow. Magneto-elastic ribbon 55 is disposed within the fluid 21. It is preferably fixed to the pipe or container containing the fluid under inspection. It may be fixed with attaching or clamping means. In FIG. 5A, clamping means 65 are schematically shown. Besides, ribbon 55 is surrounded by coil 53. In series with coil 53, coil 54 is disposed. The dots and crosses in the view represent the direction of the coils winding. Both coils 53, 54 are surrounded by coil 51, which in turn is surrounded by coil 57. The area 27 towards which ferromagnetic particles present in the fluid 21 are attracted is located substantially at the center (within the winding of coil 57. The alternating magnetic field generated in the primary coil 51 excites the magnetoelastic material 55 and produces magnetoelastic resonance.

Figure 5B:
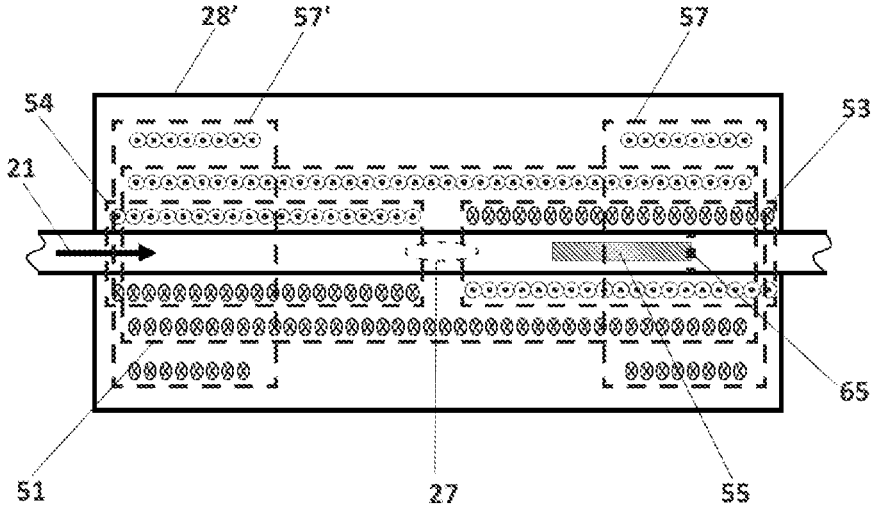
FIG. 5B shows a cross-sectional view of an alternative implementation of magnetic means.

FIG. 5B shows an alternative embodiment of apparatus 28', in which there are two bias coils 57, 57' instead of only one. Sing two coils 57, 57' may simplify the design of the system 1, 11, or of the magnetic means 28', since it facilitates implementation and access to the area 27 towards which ferromagnetic particles present in the fluid 21 are attracted. By correctly disposing coils 57, 57' at substantially the same distance with respect to this area 27, ferromagnetic particles are attracted towards are 27.

For example, magneto-elastic strip 55 may be made of the commercial material Vitrovac4040®, which has nominal composition Fe39Ni39Mo4Si6B12. When it is provided in stripe form, with a size of 30 mm×6 mm, it has a magnetoelastic resonance in 32 KHz and an anti-resonance in 36 KHz for an oil viscosity of 32.4 cSt, measured at room temperature. The excitation, done with coil 51, in the example is done between 20 KHz and 40 KHz with alternating current source 52.

The viscosity of the fluid 21 is measured in system 1, 11 as follows with the apparatus 28' (FIG. 1, 2A-2D or 4):

First, the bias field is set in an optimum point. The bias field can vary depending on the material, size and shape of the magneto-elastic strip 55. For example, in the case of the Vitrovac 4040®, it is set to 535 Am-1.

Then, a sweep between the reference frequencies (between lower and upper frequencies) for the magnetoelastic material 55 is done in excitation coil 51, exciting the magneto-elastic material. In the case of the Vitrovac 4040® the sheep is done between 20 KHz and 40 KHz.

The answer in detection coil 53 is then measured. In particular, nominal values of the voltage at a respective plurality of frequencies previously defined are measured at voltmeter 56. From the set of measured voltage and frequency values, at least one of the following parameters is extracted: the amplitude of the magnetoelastic resonance, the amplitude of the anti-resonance, the frequency of the magnetoelastic resonance, the amplitude of the anti-resonance, the damping of the magnetoelastic resonance curve and the damping of the magnetoelastic anti-resonance curve. Preferably, all these parameters are extracted. From at least one of these parameters, the viscosity of the fluid 21 is calculated by applying conventional means which are out of the scope of the present disclosure.

These measurements are repeated, either periodically or non-periodically. Thus, the evolution in time of the fluid viscosity is calculated and recorded.

In sum, the system for inspecting a fluid of the present disclosure enables the detection and counting of particles, both ferromagnetic and non-ferromagnetic ones, as well as the determination of the viscosity of the fluid under inspection. All these measurements contribute to early detection of premature failures, preventing more serious faults in the components of the machinery lubricated by the fluid under inspection.

Throughout this document, the word "comprises" and variants thereof (such as "comprising", etc.) must not be interpreted as having an exclusive meaning, in other words, they do not exclude the possibility of what is being described incorporating other elements, steps, etc.

At the same time, the disclosure is not limited to the specific embodiments described herein and also extends, for example, to variants that may be embodied by an average person skilled in the art (for example, with regard to the choice of materials, dimensions, components, configuration, etc.), within the scope of what is inferred from the claims.

The invention claimed is:

1. A system for inspecting a fluid, the system comprising:
   a lighting system for illuminating a fluid under inspection in an image detection area;
   an image capture system for capturing a sequence of images of the fluid in the image detection area;
   magnetic means for generating a magnetic field towards the image fluid under inspection, the magnetic means comprising at least one coil for generating the magnetic field, such that ferromagnetic particles in the fluid under inspection are prevented from reaching, or removed from, the image detection area;
   wherein the image capture system is configured to capture an image of the fluid located in the image detection area before the magnetic field is applied and an image of the fluid located in the image detection area after the magnetic field is applied, the image detection area being therefore free of ferromagnetic particles; and processing means configured to compare said images of the fluid under inspection and count the ferromagnetic particles in the fluid.

2. The system of claim 1, further comprising a diffuser situated between the lighting system and the fluid under inspection, the diffuser configured to provide homogeneous lighting to the area to be illuminated.

3. The system of claim 1, further comprising a lens situated between the image capture system and the fluid under inspection, the lens configured to focus the captured images.

4. The system of claim 1, wherein the magnetic means further comprises measuring means configured to measure viscosity by implementing a micro-vibration based technique.

5. The system of claim 4, wherein the magnetic means comprises:

a first coil configured to generate an alternating magnetic field;

a magnetoelastic strip submerged in the fluid under inspection and configured to be excited by the alternating magnetic field generated by the first coil to produce magnetoelastic resonance;

a second coil in which voltages related to the magnetoelastic resonance of the magnetoelastic strip are induced within a range of frequencies; and measuring means configured to measure said induced voltages at said range of frequencies;

wherein the processing means is further configured to obtain the viscosity of the fluid from at least one parameter obtained from said induced voltages and frequencies, said at least one parameter being one of: the amplitude of the magnetoelastic resonance, the amplitude of a magnetoelastic antiresonance of the magnetoelastic strip, the frequency of the magnetoelastic resonance, frequency of the magnetoelastic antiresonance, the damping of the magnetoelastic resonance curve and the damping of the magnetoelastic antiresonance curve.

6. The system of claim 5, further comprising a compensation coil for suppressing magnetic noise generated by the first coil.

7. The system of claim 6, wherein the compensation coil is disposed in series, but wounded in the opposite direction, with the second coil.

8. The system of claim 5, further comprising at least one additional coil for setting the bias field for the magnetoelastic strip.

9. The system of claim 8, wherein the coil for generating the magnetic field towards the fluid under inspection for attracting ferromagnetic particles, is the at least one additional coil of the measuring means.

10. The system of claim 8, wherein the magneto-elastic strip is surrounded by the second coil, which in turn is surrounded by the first coil, which in turn is surrounded by the at least one additional coil.

11. A method for inspecting a fluid within a detection area, the method including the following steps:

illuminating a detection area having a fluid having particles suspended therein;

capturing an image of the fluid in the detection area;

generating a magnetic field towards the detection area, in such a way that ferromagnetic particles in the fluid are removed from, or prevented from reaching, the detection area;

capturing an image of the fluid free of ferromagnetic particles in the detection area; and comparing said images of the fluid and counting the ferromagnetic particles in the fluid.

12. The method of claim 11, further comprising measuring the viscosity of the fluid as follows:

generating an alternating magnetic field at a first coil;

exciting a magnetoelastic strip submerged in the fluid under inspection, thus producing magnetoelastic resonance;

in a second coil, inducing voltages related to the magnetoelastic resonance of the magnetoelastic strip within a range of frequencies;

measuring said induced voltages at said range of frequencies; and obtaining the viscosity of the fluid from at least one parameter obtained from said induced voltages and frequencies, said at least one parameter being one of: the amplitude of the magnetoelastic resonance, the amplitude of a magnetoelastic antiresonance of the magnetoelastic strip, the frequency of the magnetoelastic resonance, frequency of the magnetoelastic antiresonance, the damping of the magnetoelastic resonance curve and the damping of the magnetoelastic antiresonance curve.

* * * * *